US011872288B2

(12) United States Patent
Hemmerle (10) Patent No.: US 11,872,288 B2
(45) Date of Patent: Jan. 16, 2024

(54) TNF-ALPHA IMMUNOCONJUGATE THERAPY FOR THE TREATMENT OF BRAIN TUMORS (71) Applicant: PHILOGEN S.P.A, Siena (IT)

(72) Inventor: Theresa Hemmerle, Otelfingen (CH)

(73) Assignee: PHILOGEN S.P.A.

( * ) Notice: Subject to any disclaimer, the term of this patent is extended or adjusted under 35 U.S.C. 154(b) by 0 days.

(21) Appl. No.: 17/999,444

(22) PCT Filed: May 24, 2021

(86) PCT No.: PCT/EP2021/063758
§ 371 (c)(1),
(2) Date: Nov. 21, 2022

(87) PCT Pub. No.: WO2021/234178
PCT Pub. Date: Nov. 25, 2021

(65) Prior Publication Data
US 2023/0233702 A1 Jul. 27, 2023

(30) Foreign Application Priority Data
May 22, 2020 (EP) .................................. 20176157

(51) Int. Cl.
A61K 39/395 (2006.01)
A61K 39/00 (2006.01)
A61K 47/68 (2017.01)
A61P 35/00 (2006.01)

(52) U.S. Cl.
CPC .......... A61K 47/6813 (2017.08); A61P 35/00 (2018.01); A61K 2039/505 (2013.01)

(58) Field of Classification Search
None
See application file for complete search history.

(56) References Cited

U.S. PATENT DOCUMENTS

2020/0253943 A1* 8/2020 Bernardes ........ G01N 33/57492

FOREIGN PATENT DOCUMENTS

| CN | 1612895 A | 5/2005 | |
|---|---|---|---|
| CN | 101437847 A | 5/2009 | |
| EP | 0 120 694 A2 | 10/1984 | |
| EP | 0 125 023 A1 | 11/1984 | |
| WO | 92/01047 A1 | 1/1992 | |
| WO | 01/62298 A2 | 8/2001 | |
| WO | WO-0162298 A2 * | 8/2001 | ........... A61K 31/704 |
| WO | 03/076469 A2 | 9/2003 | |
| WO | 2005/023318 A1 | 3/2005 | |
| WO | 2006/026348 A1 | 3/2006 | |
| WO | 2018/011404 A1 | 1/2018 | |
| WO | WO-2018011404 A1 * | 1/2018 | ........... A61K 31/704 |

OTHER PUBLICATIONS

NextSource Biotechnology LLC. (2018). Gleostine carmustine capsule gelatin coated: Highlights of prescribing information. Retrieved from: https://dailymed.nlm.nih.gov/dailymed/fda/fdaDrugXsl.cfm?setid=7f77526b-4c40-409c-82ea-d0f934d89cc2&type=display. pp. 1-16. (Year: 2018).*
NextSource Biotechnology LLC. (2016). NextSource Biotechnology Gains FDA Approval for New 5 mg Strength ofGleostine® (Lomustine), an Anti-CancerChemotherapy Agent. pp. 1-3 (Year: 2016).*
NextSource Biotechnology LLC. (2014). NextSource BiotechnologyAnnounces FDA Short Supplyrelease of the formally known BristolMyers Squibb (CeeNu®) BrandOncology product now currentlymarketed under the NextSourceBiotechnology Lomustine (CCNU)label Exclusively in the United States. p. 1-4. (Year: 2014).*
ClinicalTrials NCT03779230Safety and Efficacy of L19TNF in Patients With Isocitrate Dehydrogenase (IDH) Wildtype WHO Grade III / IV Glioma at First Re(GLIOMOON). Mar. 19, 2019. pp. 1-5. (Year: 2019).*
Weiss et al. Immunocytokines are a novel immunotherapeutic approach against glioblastoma. Neuro-Oncology, 21 (supp 3) p. iii61. Abstract No. P12.08, Aug. 2019 (Year: 2019).*
Look et al. Lomustine and the Immunocytokine L19TNF Are a Promising Treatment Combination for Recurrent Glioblastoma. abstract OS08.7.A. Neuro-Oncology, vol. 24, Issue Supplement_2, Sep. 2022, pp. ii19-ii20. (Year: 2022).*
Look et al. The Combination of Lomustine and the Immunocytokine L19TNF is a Promising Treatment for Recurrent Glioblastoma. Abstract CTIM-22, Neuro-Oncology (IF 15.9) Pub Date: Nov. 14, 2022. (Year: 2022).*
Written Opinion of the International Searching Authority, completed Jul. 31, 2021, issued in corresponding International Application No. PCT/EP2021/063758.
International Preliminary Report on Patentability, completed Dec. 6, 2021, issued in corresponding International Application No. PCT/EP2021/063758.
International Search Report, dated Oct. 8, 2021, issued in corresponding International Application No. PCT/EP2021/063758.
Roth, Patrick et al., "Targeting glioblastoma with novel immunocytokines," Journal of Clinical Oncology, vol. 38, No. 15_suppl, May 20, 2020, p. 2558-2558.
Weiss, Tobias et al., "History of Changes for Study: NCT03779230 Version 3," Jun. 25, 2019, Retrieved from the Internet: URL:https://clinicaltrials.gov/ct2/history/NCT03779230?V3=View#StudyPageTop, Retrieved on Jun. 30, 2021.
Weiss, Tobias et al., "Immunocytokines are a promising immunotherapeutic approach against glioblastoma," Science Translational Medicine, vol. 12, No. 564, Oct. 7, 2020, eabb2311, pp. 1-11.

(Continued)

Primary Examiner — Maher M Haddad
(74) Attorney, Agent, or Firm — Kathleen D. Rigaut; Howson & Howson LLP (57) ABSTRACT The present invention relates to immunoconjugates, compositions, methods and uses for treating brain tumors, especially glioma, by administration of a tumour necrosis factor alpha (TNFα) immunoconjugate.

16 Claims, 4 Drawing Sheets
Specification includes a Sequence Listing.

(56) References Cited

OTHER PUBLICATIONS

Notice of Reasons for Rejection, dated Apr. 12, 2023, issued in corresponding Japanese Patent Application No. 2022-570616.
Puca, E. et al., "Comparative evaluation of bolus and fractionated administration modalities for two antibody-cytokine fusions in immunocompetent tumor-bearing mice," Journal of Controlled Release, vol. 317, Nov. 2019, pp. 282-290.
Corbellari, R. et al., "The immunocytokine L19-TNF eradicates Sarcomas in combination with Chemotherapy agents or with immune check-point inhibitors," bioRxiv, Feb. 4, 2020, pp. 1-24.
Menssen, H.D. et al., "Antibody-based delivery of tumor necrosis factor (L19-TNFα) and interleukin-2 (L19-IL2) to tumor-associated blood vessels has potent immunological and anticancer activity in the syngeneic J558L BALB/c myeloma model," Journal of Cancer Research and Clinical Oncology, vol. 144, 2018, pp. 499-507.
First Office Action, dated Jul. 29, 2023, issued in corresponding Chinese Patent Application No. 2202180036945.7.
Xiong Fangwu et al., "Lomustine," Chinese Clinical Drug Dictionary (Chemical Medicine) (1st volume), published Aug. 31, 2018, China Medical Science and Technology Press.

* cited by examiner

VH (SEQ ID NO: 7)

CDR1          CDR2

EVQLLESGGGLVQPGGSLRLSCAASGFTFS<u>SFSMS</u>WVRQAPGKGLEWVS<u>SISGSS</u>

CDR3

<u>GTTYYADSVKG</u>RFTISRDNSKNTLYLQMNSLRAEDTAVYYCAK<u>PFPYFDY</u>WGQGT

LVTVSS

LINKER (SEQ ID NO: 8)

GDGSSGGSGGAS

VL (SEQ ID NO: 9)

CDR1          CDR2

EIVLTQSPGTLSLSPGERATLSC<u>RASQSVSSSFLA</u>WYQQKPGQAPRLLIY<u>YASSR</u>

CDR3

<u>AT</u>GIPDRFSGSGSGTDFTLTISRLEPEDFAVYYC<u>QQTGRIPPT</u>FGQGTKVEIK

Figure 3

SEQUENCE LISTING

```
<160> NUMBER OF SEQ ID NOS: 13

<210> SEQ ID NO 1
<211> LENGTH: 5
<212> TYPE: PRT
<213> ORGANISM: Artificial Sequence
<220> FEATURE:
<223> OTHER INFORMATION: synthetic construct

<400> SEQUENCE: 1

Ser Phe Ser Met Ser
1               5

<210> SEQ ID NO 2
<211> LENGTH: 17
<212> TYPE: PRT
```

```
<213> ORGANISM: Artificial Sequence
<220> FEATURE:
<223> OTHER INFORMATION: synthetic construct

<400> SEQUENCE: 2

Ser Ile Ser Gly Ser Ser Gly Thr Thr Tyr Tyr Ala Asp Ser Val Lys
1               5                   10                  15

Gly

<210> SEQ ID NO 3
<211> LENGTH: 7
<212> TYPE: PRT
<213> ORGANISM: Artificial Sequence
<220> FEATURE:
<223> OTHER INFORMATION: synthetic construct

<400> SEQUENCE: 3

Pro Phe Pro Tyr Phe Asp Tyr
1               5

<210> SEQ ID NO 4
<211> LENGTH: 12
<212> TYPE: PRT
<213> ORGANISM: Artificial Sequence
<220> FEATURE:
<223> OTHER INFORMATION: synthetic construct

<400> SEQUENCE: 4

Arg Ala Ser Gln Ser Val Ser Ser Ser Phe Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: synthetic construct

<400> SEQUENCE: 5

Tyr Ala Ser Ser Arg Ala Thr
1               5

<210> SEQ ID NO 6
<211> LENGTH: 9
<212> TYPE: PRT
<213> ORGANISM: Artificial Sequence
<220> FEATURE:
<223> OTHER INFORMATION: synthetic construct

<400> SEQUENCE: 6

Gln Gln Thr Gly Arg Ile Pro Pro Thr
1               5

<210> SEQ ID NO 7
<211> LENGTH: 116
<212> TYPE: PRT
<213> ORGANISM: Artificial Sequence
<220> FEATURE:
<223> OTHER INFORMATION: synthetic construct

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30
```

```
Ser Met Ser Trp Val Arg Gln Ala Pro Gly Lys Gly Leu Glu Trp Val
            35                  40                  45

Ser Ser Ile Ser Gly Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser
        115

<210> SEQ ID NO 8
<211> LENGTH: 12
<212> TYPE: PRT
<213> ORGANISM: Artificial Sequence
<220> FEATURE:
<223> OTHER INFORMATION: synthetic construct

<400> SEQUENCE: 8

Gly Asp Gly Ser Ser Gly Gly Ser Gly Gly Ala Ser
1               5                   10

<210> SEQ ID NO 9
<211> LENGTH: 108
<212> TYPE: PRT
<213> ORGANISM: Artificial Sequence
<220> FEATURE:
<223> OTHER INFORMATION: synthetic construct

<400> SEQUENCE: 9

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Tyr Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Gly Arg Ile Pro
                85                  90                  95

Pro Thr Phe Gly Gln Gly Thr Lys Val Glu Ile Lys
            100                 105

<210> SEQ ID NO 10
<211> LENGTH: 236
<212> TYPE: PRT
<213> ORGANISM: Artificial Sequence
<220> FEATURE:
<223> OTHER INFORMATION: synthetic construct

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
```

```
                35                  40                  45
Ser Ser Ile Ser Gly Ser Ser Gly Thr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Phe Pro Tyr Phe Asp Tyr Trp Gly Gln Gly Thr Leu Val
                100                 105                 110

Thr Val Ser Ser Gly Asp Gly Ser Gly Gly Ser Gly Gly Ala Ser
                115                 120                 125

Glu Ile Val Leu Thr Gln Ser Pro Gly Thr Leu Ser Leu Ser Pro Gly
            130                 135                 140

Glu Arg Ala Thr Leu Ser Cys Arg Ala Ser Gln Ser Val Ser Ser Ser
145                 150                 155                 160

Phe Leu Ala Trp Tyr Gln Gln Lys Pro Gly Gln Ala Pro Arg Leu Leu
                165                 170                 175

Ile Tyr Tyr Ala Ser Ser Arg Ala Thr Gly Ile Pro Asp Arg Phe Ser
                180                 185                 190

Gly Ser Gly Ser Gly Thr Asp Phe Thr Leu Thr Ile Ser Arg Leu Glu
            195                 200                 205

Pro Glu Asp Phe Ala Val Tyr Tyr Cys Gln Gln Thr Gly Arg Ile Pro
        210                 215                 220

Pro Thr Phe Gly Gln Gly Thr Lys Val Glu Ile Lys
225                 230                 235

<210> SEQ ID NO 11
<211> LENGTH: 157
<212> TYPE: PRT
<213> ORGANISM: Artificial Sequence
<220> FEATURE:
<223> OTHER INFORMATION: synthetic construct

<400> SEQUENCE: 11

Val Arg Ser Ser Ser Arg Thr Pro Ser Asp Lys Pro Val Ala His Val
 1               5                  10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
                35                  40                  45

Val Val Pro Ser Glu Gly Leu Tyr Leu Ile Tyr Ser Gln Val Leu Phe
 50                  55                  60

Lys Gly Gln Gly Cys Pro Ser Thr His Val Leu Leu Thr His Thr Ile
 65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
                100                 105                 110

Pro Trp Tyr Glu Pro Ile Tyr Leu Gly Gly Val Phe Gln Leu Glu Lys
            115                 120                 125

Gly Asp Arg Leu Ser Ala Glu Ile Asn Arg Pro Asp Tyr Leu Asp Phe
        130                 135                 140

Ala Glu Ser Gly Gln Val Tyr Phe Gly Ile Ile Ala Leu
145                 150                 155
```

<210> SEQ ID NO 12
<211> LENGTH: 17
<212> TYPE: PRT
<213> ORGANISM: Artificial Sequence
<220> FEATURE:
<223> OTHER INFORMATION: synthetic construct

<400> SEQUENCE: 12

```
Glu Phe Ser Ser Ser Gly Ser Ser Ser Gly Ser Ser Ser
1               5                   10                  15

Gly
```

<210> SEQ ID NO 13
<211> LENGTH: 410
<212> TYPE: PRT
<213> ORGANISM: Artificial Sequence
<220> FEATURE:
<223> OTHER INFORMATION: synthetic construct

<400> SEQUENCE: 13

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Gly Gly Ser Gly Gly Ala Ser
            115                 120                 125

Glu Ile Val Leu Thr Gln Ser Pro Gly Thr Leu Ser Leu Ser Pro Gly
130                 135                 140

Glu Arg Ala Thr Leu Ser Cys Arg Ala Ser Gln Ser Val Ser Ser Ser
145                 150                 155                 160

Phe Leu Ala Trp Tyr Gln Gln Lys Pro Gly Gln Ala Pro Arg Leu Leu
                165                 170                 175

Ile Tyr Tyr Ala Ser Ser Arg Ala Thr Gly Ile Pro Asp Arg Phe Ser
            180                 185                 190

Gly Ser Gly Ser Gly Thr Asp Phe Thr Leu Thr Ile Ser Arg Leu Glu
        195                 200                 205

Pro Glu Asp Phe Ala Val Tyr Tyr Cys Gln Gln Thr Gly Arg Ile Pro
    210                 215                 220

Pro Thr Phe Gly Gln Gly Thr Lys Val Glu Ile Lys Glu Phe Ser Ser
225                 230                 235                 240

Ser Ser Gly Ser Ser Ser Gly Ser Ser Ser Gly Val Arg Ser
                245                 250                 255

Ser Ser Arg Thr Pro Ser Asp Lys Pro Val Ala His Val Val Ala Asn
            260                 265                 270

Pro Gln Ala Glu Gly Gln Leu Gln Trp Leu Asn Arg Arg Ala Asn Ala
        275                 280                 285

Leu Leu Ala Asn Gly Val Glu Leu Arg Asp Asn Gln Leu Val Val Pro
```

-continued

```
            290                 295                 300
Ser Glu Gly Leu Tyr Leu Ile Tyr Ser Gln Val Leu Phe Lys Gly Gln
305                 310                 315                 320

Gly Cys Pro Ser Thr His Val Leu Leu Thr His Thr Ile Ser Arg Ile
                325                 330                 335

Ala Val Ser Tyr Gln Thr Lys Val Asn Leu Leu Ser Ala Ile Lys Ser
                340                 345                 350

Pro Cys Gln Arg Glu Thr Pro Glu Gly Ala Glu Ala Lys Pro Trp Tyr
                355                 360                 365

Glu Pro Ile Tyr Leu Gly Gly Val Phe Gln Leu Glu Lys Gly Asp Arg
        370                 375                 380

Leu Ser Ala Glu Ile Asn Arg Pro Asp Tyr Leu Asp Phe Ala Glu Ser
385                 390                 395                 400

Gly Gln Val Tyr Phe Gly Ile Ile Ala Leu
                405                 410
```

TNF-ALPHA IMMUNOCONJUGATE THERAPY FOR THE TREATMENT OF BRAIN TUMORS

CROSS REFERENCE TO RELATED APPLICATION

This application is a § 371 of International Application No. PCT/EP2021/063758, filed May 24, 2021, which claims priority to EP Application No. 20176157.4 filed May 22, 2020, the entire disclosure of each being incorporated herein by reference as though set forth in full.

FIELD OF THE INVENTION

The present invention relates to immunoconjugates, compositions, methods and uses for treating brain tumors, especially glioma, by administration of a tumour necrosis factor alpha (TNFα) immunoconjugate.

BACKGROUND TO THE INVENTION

Brain tumors comprise primary and secondary tumors. Primary brain tumors are neoplasms that originate from cells of the brain or meninges, in contrast to secondary brain tumors such as brain metastases or malignant lymphomas (PCNSL), which originate outside the central nervous system (CNS).

Glioma is a type of tumor that occurs in the brain and spinal cord and starts in the glial cells of the brain or the spine. A glioma can affect brain function and be live threatening, depending on its location and rate of growth. Gliomas along with meningiomas, are the most common types of primary brain tumors. They are classified histologically according to the type of glial cell involved in the tumorigenesis (astrocytes, oligodendrocytes, ependymal cells) and molecularly according to genetic features, which can help predict how the tumor will behave over time and which treatments are most likely to work.

Gliomas are graded according to the four-tiered WHO system ranging from grade I to IV, indicating malignancy.

Grade I: slow growing, well-demarcated tumors with favourable prognosis

Grade II: slow growing tumors often with brain invasive growth that precludes complete resection Grade III: rapidly growing high-grade tumors with features of anaplasia, particularly high cellularity, cellular pleomorphism, increased nuclear atypia and brisk mitotic activity Grade IV ("glioblastoma"): most malignant gliomas which show the characteristics of grade III and additional pathological microvascular proliferation and areas of necrosis.

The cornerstone of glioma therapy is the greatest possible but non-functional resection, which can be curative in the case of WHO grade I glioma. For diffuse WHO grade II to IV gliomas, a macroscopically complete resection is often possible, but the diffuse infiltrating character of the disease means that this is usually not a curative resection. In gliomas, the extent of resection is a prognostic factor. Postoperative radiotherapy (RT) improves survival, the time of RT may vary according to risk factors and WHO grade. The third pillar of therapy is drug-based tumor therapy. Predictive markers are LOH1p/19q status and MGMT promoter methylation.

A variety of treatments including radiotherapy or radiosurgery, surgery, chemotherapy or combination of these options as well as supportive care are available for patients with no response or progression after initial therapy, but survival is highly variable on an individual basis. Patients with adequate performance status that have not received prior cytotoxic therapy may benefit from chemotherapy. Upon tumor recurrence, treatment options include supportive care, reoperation, re-irradiation, systemic therapies and combined modality therapy. Several options are available for second-line chemotherapy, but no standard of care has been established.

Despite the available therapy options, glioma remains a life-threatening disease. While the 5-year relative survival rate for all cancers combined in the United States was 69% between 2008 and 2014, the 5-year relative survival rate for brain and other nervous system cancers in the same period was only 35%. High grade glioma and especially glioblastoma is one of the most challenging to treat cancers with a very poor prognosis and a median survival in the range of only 16 months with standard of care treatment. Because of the poor prognosis and the limited treatment options for these patients, novel treatment options are urgently needed.

Tumour necrosis factor alpha (TNFα) is a cytokine produced by many cell types, mainly activated monocytes and macrophages. It is expressed as a 26 kDa integral transmembrane precursor protein from which a mature protein of approximately 17 kDa is released by proteolytic cleavage. The soluble bioactive TNFα is a homotrimer that binds cell surface receptors. TNFα has been shown to induce necrosis of solid tumours. It exerts its effects mainly on the endothelium of the tumour-associated vasculature, with increased permeability, upregulation of tissue factor, fibrin deposition and thrombosis, and massive destruction of the endothelial cells.

WO2001/062298, which is hereby incorporated by reference in its entirety, described immunoconjugates comprising TNFα, fused to antibody L19. L19 specifically binds the ED-B domain of fibronectin isoform B-FN, which is one of the best-known markers of angiogenesis (U.S. Pat. No. 8,097,254). ED-B is an extra domain of 91 amino acids found in the B-FN isoform and is identical in mouse, rat, rabbit, dog and man. B-FN accumulates around neovascular structures in aggressive tumours and other tissues undergoing angiogenesis, such as the endometrium in the proliferative phase and some ocular structures in pathological conditions but is otherwise undetectable in normal adult tissues.

SUMMARY OF THE INVENTION

The present inventors have determined that the administration of immunoconjugates comprising TNFα and can be used to successfully treat brain tumors.

Accordingly, one aspect of the invention provides a method of treating a brain tumor by administering a TNFα immunoconjugate to the patient.

In another aspect, the invention provides a TNFα immunoconjugate for use in a method of treating a brain tumor in a patient, the method comprising administering the TNFα immunoconjugate to the patient.

In yet another aspect, the invention provides the use of a TNFα immunoconjugate in the manufacture of a medicament for the treatment of a brain tumor in a patient, the treatment comprising administering the TNFα immunoconjugate.

In preferred embodiments, the brain tumor is a glioma. The glioma may be a Grade III/IV glioma. The glioma may be an isocitrate dehydrogenase (IDH) wildtype glioma. In some embodiments, the Grade III/IV glioma is at first relapse when the treatment is administered. In some embodiments, the glioma is a Grade IV glioblastoma. Optionally, the Grade IV glioblastoma may be newly diagnosed when the treatment is administered. Optionally, the Grade IV glioblastoma may be at first relapse when the treatment is administered.

In preferred embodiments, the TNFα immunoconjugate comprises TNFα linked to an antibody molecule that binds to a splice isoform of an extracellular matrix component. The splice isoform of fibronectin may be B-FN.

In preferred embodiments, the TNFα immunoconjugate comprises TN Fa linked to an antibody molecule comprising L19 complementarity determining regions (CDRs), wherein the amino acid sequences of the CDRs correspond with those set forth in SEQ ID NOs: 1-6. In some embodiments, the antibody molecule comprises the L19 VH domain SEQ ID NO: 7 and the L19 VL domain SEQ ID NO: 9. In some embodiments, the TNFα immunoconjugate comprises TNFα linked to an antibody molecule which is a single chain Fv (scFv), optionally wherein the antibody molecule is L19 (scFv) SEQ ID NO: 10. The TNFα immunoconjugate may have the amino acid sequence of SEQ ID NO: 13.

The treatments disclosed herein typically involve the administration of the immunoconjugate by intravenous injection. Alternatively, the immunoconjugate can be administered by intratumoural or intrathecal injection.

In addition to immunoconjugate administration, in some embodiments, the immunoconjugate is administered in combination with radiotherapy and/or in combination with another anticancer agent, e.g. a chemotherapy.

In some embodiments, the immunoconjugate is administered in combination with a chemotherapy. The chemotherapy may be an alkylating agent. The alkylating agent may be lomustine. The lomustine may be administered at a dose that is within the range of 50-200 mg/m$^2$, or 75-150 mg/m$^2$. The lomustine may be administered at a dose of about 80, about 90, about 100, or about 110 mg/m$^2$. Preferably, lomustine is administered at a dose of between about 90 and about 110 mg/m$^2$. In some embodiments, the lomustine is administered at a dose of about 90 mg/m$^2$. Combination therapies involving lomustine may be particularly useful for treating a glioblastoma at first relapse.

In some embodiments, the chemotherapy (alkylating agent) is temozolomide (TMZ). The TMZ may be administered at a dose that is within the range of 50-300 mg/m$^2$, or 75-200 mg/m$^2$. Combination treatments, e.g. those involving TMZ, may involve radiotherapy as well. For instance, the radiotherapy can be administered at daily fractions of 2 Gy (a total of 60 Gy in 30 fractions). When TMZ is administered in combination with radiotherapy, TMZ it is preferably administered at 75 mg/m$^2$ or at doses between 150 and 200 mg/m$^2$ in the maintenance setting. Combination therapies involving TMZ and radiotherapy may be particularly useful for treating a newly diagnosed glioblastoma.

When administered in combination with lomustine, L19-TNFα can be given at doses between 5 and 20 µg/Kg, preferably between 8 and 15 µg/Kg, more preferably between 10 and 13 µg/Kg. When administered in combination with TMZ, L19-TNFα can be given at doses of between 5 and 20 µg/Kg, preferably between 6 and 15 µg/Kg, more between 7 and 13 µg/Kg.

When administered without chemotherapy (i.e., as a monotherapy, or in combination with radiotherapy alone), L19-TNFα can be given at doses between 5 and 20 µg/Kg, preferably between 6 and 18 µg/Kg, between 7 and 17 µg/Kg or between 8 and 15 µg/Kg, more preferably between 10 and 13 µg/Kg.

The skilled person will understand that the TNFα immunoconjugate may be administered just once in the context of the medical uses and treatments of the present invention. Alternatively, the medical uses and treatments of the present invention may involve multiple administrations of the TNFα immunoconjugate. In some embodiments, the medical uses and treatments of the present invention may involve chemotherapy, radiotherapy and/or surgery (each of which may be performed before, concurrently with, or after TNFα immunoconjugate administration).

In some embodiments, following the medical uses and/or treatments of the present invention (which involve the TNFα immunoconjugate being administered to the patient, as disclosed herein), tumor necrosis can be observed after TNFα immunoconjugate administration. In some cases, tumor necrosis is detectable a day after the TNFα immunoconjugate was administered. Thus, the medical uses and methods of the invention can optionally include the step of sending the patient for an evaluation of tumor necrosis at a timepoint after TNFα immunoconjugate administration, e.g. 1 day after, 2 days after, 3 days after, 4 days after, 5 days after, 6 days after, about a week after, about 10 days after, about two weeks after or about a month after the TN Fa immunoconjugate is administered. Thus, the medical uses and methods of the invention can also include taking a decision regarding further therapy, and optionally performing said further therapy, after viewing the results of the evaluation of tumor necrosis. Preferably, tumor necrosis will be observed at one or more of these time points. The skilled person is readily able to use techniques such as perfusion MRI to measure tumor necrosis. Perfusion MRI can discriminate between dead tumor areas and live regions of tumor cells; this technique can be applied to the present clinical setting. Further therapy may comprise further administration of the medical uses and/or treatments of the present invention. Additionally, or alternatively, further therapy may comprise chemotherapy, radiotherapy and/or surgery.

In some embodiments, following the medical uses and/or treatments of the present invention (which involve the TNFα immunoconjugate being administered to the patient, as disclosed herein), a reduction of blood perfusion to the tumor can be observed after TNFα immunoconjugate administration. In some cases, a reduction of blood perfusion to the tumor is detectable a day after the TNFα immunoconjugate is administered to the patient. Thus, the medical uses and methods of the invention can optionally include the step of sending the patient for observation of tumor blood perfusion at a timepoint after TNFα immunoconjugate administration, e.g. 1 day after, 2 days after, 3 days after, 4 days after, 5 days after, 6 days after, about a week after, about 10 days after, about two weeks after or about a month after the TNFα immunoconjugate is administered. Preferably, a reduction of blood perfusion will be observed at one or more of these time points. The medical uses and methods of the invention can also include the subsequent step of taking a decision regarding further therapy, and optionally performing said further therapy, after viewing the results of the tumor blood perfusion observation. The skilled person is readily able to use techniques such as perfusion MRI to perform this observation. Perfusion MRI is a common method of monitoring brain tumors; and can be applied to the present clinical setting. Further therapy may comprise further administration of the medical uses and/or treatments of the present invention. Additionally, or alternatively, further therapy may comprise chemotherapy, radiotherapy and/or surgery.

In some embodiments of the medical uses and/or treatments of the present invention (which involve the TNFα immunoconjugate being administered to the patient, as disclosed herein), surgery can be performed on the brain tumor. In some embodiments, some of the tumor has been removed prior to the medical use/method of the present invention being performed. In some embodiments, some, or all of the tumor will be removed after the medical uses and/or treatments of the present invention are performed.

In some embodiments, following the medical uses and/or treatments of the present invention (which involve the TNFα immunoconjugate being administered to the patient, as disclosed herein), infiltration of T cells into the tumor tissue can be observed after TNFα immunoconjugate administration. The detection of T cell infiltration can be achieved by immunohistochemistry performed on a tumor sample obtained via surgery. The infiltrating T cells may be CD4+ T cells (so called 'helper T cells') and/or CD8+ T cells (so called 'cytotoxic T cells'). In some embodiments of the invention, surgery precedes and follows TNFα immunoconjugate administration (e.g. with chemo/radiotherapy). In these embodiments, the extent of T cell infiltration before TNFα immunoconjugate administration can be compared with the extent of T cell infiltration after TNFα immunoconjugate administration. In some embodiments, the increase of T cell infiltration can be observed in CD4+ T cell count. In some embodiments, the increase of T cell infiltration can be observed in CD8+ T cell count. The skilled person is readily able to use techniques such as immunohistochemistry, or flow cytometry, to detect and count T cells in a sample. Appropriate reagents are widely available. Such techniques involve using anti-T cell antibodies to stain the T cells in a mixed-cell sample.

Figure 2:
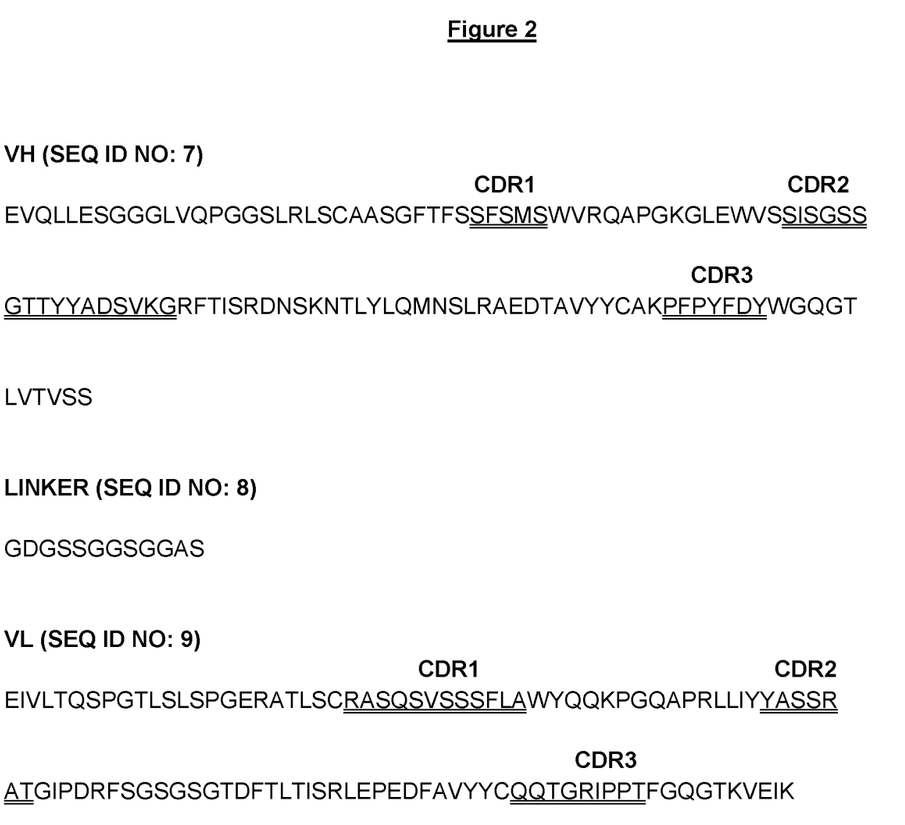
FIG. 2 shows the amino acid sequence of L19(scFv) (SEQ ID NO: 10). The VH and VL domains are shown separately (SEQ ID NO: 7 and SEQ ID NO: 9, respectively). The CDR 1, 2 and 3 sequences in both the VH and VL domains are shown underlined. The VH and VL domains are linked by a 12-residue peptide linker sequence (SEQ ID NO: 8).

A number of splice isoforms of tumour extracellular matrix components are known, and antibody molecules targeting any such isoform may be used to selectively target the cancer. These include splice isoforms of fibronectin, such as B-FN. B-FN includes an extra domain ED-B, and antibody molecules of the invention are preferably targeted to this domain. A preferred antibody molecule comprises the complementarity determining regions (CDRs) of antibody L19. These are, as illustrated in FIG. 2:

|         |                   | SEQ ID NO: 1 |
|---------|-------------------|--------------|
| VH CDR 1 | SFSMS             |              |

|         |                   | SEQ ID NO: 2 |
|---------|-------------------|--------------|
| VH CDR 2 | SISGSSGTTYYADSVKG |              |

|         |                   | SEQ ID NO: 3 |
|---------|-------------------|--------------|
| VH CDR 3 | PFPYFDY           |              |

|         |                   | SEQ ID NO: 4 |
|---------|-------------------|--------------|
| VL CDR 1 | RASQSVSSSFLA      |              |

|         |                   | SEQ ID NO: 5 |
|---------|-------------------|--------------|
| VL CDR 2 | YASSRAT           |              |

|         |                   | SEQ ID NO: 6 |
|---------|-------------------|--------------|
| VL CDR 3 | QQTGRIPPT         |              |

The TNFα immunoconjugate preferably comprises TNFα linked to an antibody molecule comprising the L19 CDRs. The antibody molecule in the immunoconjugate may bind the same extracellular matrix component, optionally the same splice isoform, e.g. they may bind the same domain.

Preferably, the antibody molecule (of the TNFα immunoconjugate) comprises the L19 VH domain and/or the L19 VL domain. Amino acid sequences of the L19 VH and VL domains are SEQ ID NO: 7 and SEQ ID NO: 9 respectively (FIG. 2).

Preferably the antibody molecule is a single chain Fv (scFv) or other antibody fragment of low molecular weight and/or lacking an Fc region. These properties assist with targeting and tissue penetration of the immunoconjugate at the tumour site. A preferred antibody molecule is scFv-L19, which is an scFv comprising an L19 VH domain and an L19 VL domain, wherein the VH and VL are conjoined in a single polypeptide chain by a peptide linker sequence. The skilled person will appreciate that a wide range of linkers can be used both within the context of linking VH and VL domains; and within the context of linking the antibody domain to the TNF domain. The skilled person can readily identify linkers that can be used to retain the functionality of the domains that they are linking. The VH domain contains VH CDR1, CDR2 and CDR3 sequences, and the VL domain contains VL CDR1, CDR2 and CDR3 sequences. The VH domain may have an amino acid sequence as set out in FIG. 2 (SEQ ID NO: 7). The VL domain may have an amino acid sequence as set out in FIG. 2 (SEQ ID NO: 9). The VH and VL domains are normally joined by a peptide linker such as the 12-residue linker shown in FIG. 2 (SEQ ID NO: 8). Preferably, the scFv-L19 comprises or consists of the amino acid sequence shown in FIG. 2 (SEQ ID NO: 10).

A molecular linker such as a peptide may be used to join the cytokine to the antibody molecule, facilitating expression of all or part of the immunoconjugate as a fusion protein. Where the antibody molecule is also a single chain molecule, such as scFv, the entire immunoconjugate polypeptide chain may conveniently be produced as a fusion protein. For the TNFα immunoconjugate, the fusion proteins are then assembled into trimers, allowing TNFα to adopt its normal trimeric form.

Optionally, the immunoconjugate carries a detectable and/or functional label, such as a radioactive isotope. Radiolabelled L19, and its use in cancer therapy, has been previously described (WO2003/076469, WO2005/023318).

Optionally, the immunoconjugates are injected directly at the cancer site, i.e. at the tumour/lesion responsible for causing the cancer. In some aspects, the injection needle is inserted through an intracranial route to access the lesion.

Other treatments that may be used in combination with the invention include the administration of chemotherapy and/or radiotherapy.

In some aspects, the chemotherapy is the alkylating agent temozolomide (TMZ) or lomustine. TMZ may be administered at 75-200 mg/m$^2$. The lomustine may be administered at a dose that is within the range of 50-200 mg/m$^2$, or 75-150 mg/m$^2$. The lomustine may be administered at a dose of about 80, about 90, about 100 or about 110 mg/m$^2$. Preferably, lomustine may be administered at 90 mg/m$^2$.

In some other aspects, radiotherapy may be administered at 20-100 Gy, preferably 40-80 Gy, more preferably at 60 Gy. The radiotherapy may be fractionated. For instance, the dose may be split into fractions of about 2 Gy. In some embodiments, the radiotherapy is administered at 60 Gy/30 fractions given at 2 Gy on Days 1-5 of each week of treatment, for 6 weeks of treatment.

DETAILED DESCRIPTION OF THE INVENTION

Certain aspects of the invention are as set out in the appended claims, which may be combined with any other part of the present disclosure.

An antibody molecule is an immunoglobulin whether natural or partly or wholly synthetically produced. The term also covers any polypeptide or protein comprising an antibody antigen-binding site. Thus, this term covers antibody fragments and derivatives, including any polypeptide comprising an antibody antigen-binding site, whether natural or wholly or partially synthetic. Fusion proteins comprising an antibody antigen-binding site, or equivalent, fused to another polypeptide are therefore included. Cloning and expression of chimeric antibodies is well known (EP0120694, EP0125023).

Further techniques available in the art of antibody engineering have made it possible to isolate human and humanised antibodies. For example, human hybridomas can be made as previously described. Phage display is another established technique (WO92/01047). Transgenic mice in which the mouse antibody genes are inactivated and functionally replaced with human antibody genes while leaving intact other components of the mouse immune system can be used for isolating human antibodies.

Synthetic antibody molecules may be created by expression from genes generated by means of oligonucleotides synthesised and assembled within suitable expression vectors.

It has been shown that fragments of a whole antibody can perform the function of binding antigens. Antibody fragments are preferred in conjugates of the invention owing to their small size and minimised interaction with other molecules and receptors (e.g. Fc receptor). Particularly preferred are single chain Fv molecules (scFv), wherein a VH domain and a VL domain are linked by a peptide linker which allows the two domains to associate to form an antigen binding site. scFv may be stabilised by the incorporation of disulphide bridges linking the VH and VL domains.

Another small antigen-binding antibody fragment is a dAb (domain antibody), namely the variable region of an antibody heavy or light chain. VH dAbs occur naturally in camelids (e.g. camel, llama) and may be produced by immunising a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation.

An antigen-binding site is the part of a molecule that specifically binds to and is complementary to all or part of the target antigen. In an antibody molecule it is referred to as the antibody antigen-binding site, and comprises the part of the antibody that specifically binds to and is complementary to all or part of the target antigen. Where an antigen is large, an antibody may only bind to a particular part of the antigen, which part is termed an epitope. An antibody antigen-binding site may be provided by one or more antibody variable domains. Preferably, an antibody antigen-binding site comprises an antibody light chain variable region (VL) and an antibody heavy chain variable region (VH).

The term "specific" may be used to refer to the situation in which one member of a specific binding pair will not show any significant binding to molecules other than its specific binding partner(s). The term is also applicable where e.g. an antigen-binding site is specific for a particular epitope that is carried by a number of antigens, in which case the antibody carrying the antigen-binding site will be able to bind to the various antigens carrying the epitope.

In immunoconjugates of the invention, the antibody molecule preferably binds an extracellular matrix component which is a marker of tumour growth. The extracellular matrix (ECM) is remodeled during tumour growth, and alternative splice variants of ECM components may be selectively expressed at the site of the lesion.

One example is fibronectin. For example, the B-FN isoform of fibronectin contains an extra domain ED-B. An antibody molecule preferably binds specifically to ED-B of fibronectin isoform B-FN. The antibody molecule may comprise the L19 CDRs. For example, the antibody molecule may be a scFv having a VH domain with an amino acid sequence comprising VH CDR1, VH CDR2 and/or VH CDR3 of L19, and a VL domain with an amino acid sequence comprising VL CDR1, VL CDR2 and/or VL CDR3 of L19. An antibody molecule may comprise a VH domain having an amino acid sequence with at least 60%, 65%, 70%, 75%, 80%, 85%, 90%, 95% or 100% sequence identity with the amino acid sequence of the L19 VH domain as set out in SEQ ID NO: 7, and/or comprises a VL domain having an amino acid sequence with at least 60%, 65%, 70%, 75%, 80%, 85%, 90%, 95% or 100% sequence identity with the amino acid sequence of the L19 VL domain as set out in SEQ ID NO: 9. Preferably the antibody molecule is an scFv(L19) comprising an L19 VH domain (SEQ ID NO: 7) and an L19 VL domain (SEQ ID NO: 9). In a preferred embodiment, the antibody molecule is L19(scFv) having the amino acid sequence SEQ ID NO: 10 (FIG. 2).

Modified forms of the L19 VH and/or VL domain may be employed in immunoconjugates of the invention, for example an antibody molecule may comprise the L19 VH or L19 VL domain in which 1, 2, 3, 4 or 5 amino acid substitutions have been made in a CDR and/or framework region, while retaining specific binding to fibronectin ED-B. Such amino acid substitutions are preferably conservative, e.g. substitution of one hydrophobic residue for another, one polar residue for another, arginine for lysine, glutamic for aspartic acid, or glutamine for asparagine.

Nucleic acid molecules encoding the immunoconjugates and parts thereof also form part of the invention. The nucleic acid molecule may be a vector, e.g. a plasmid suitable for expression of the nucleotide sequence. Normally the nucleotide sequence is operably linked to a regulatory element such as a promoter for transcription.

The nucleic acid molecules may be contained in a host cell, which may be a cell cotransfected with the nucleic acid molecules or a daughter of such a cell. Cells, especially eukaryotic cells e.g. HEK and CHO cells, or bacterial cells e.g. *Escherichia coli*, containing the nucleic acid molecules also form part of the invention.

Immunoconjugates of the invention may be produced using recombinant techniques, for example by expressing all or part of the immunoconjugate as a fusion protein. Normally the expression is performed in a host cell containing nucleic acid, as described above. Expression may therefore comprise culturing such a host cell. For TNFα fusion proteins, trimerisation of the subunits may occur in the cell or during purification of the fusion proteins from the cell.

Preferably the antibody molecule is conjugated with the cytokine by means of a peptide bond, e.g. within a fusion protein comprising the TNFα and the antibody molecule or a polypeptide chain thereof. See WO2001/062298. An example of a suitable linker is set out in SEQ ID NO: 12.

TNFα used in immunoconjugates of the invention is preferably human TN Fa. The human TNFα preferably comprises or consists of the amino acid sequence set out in SEQ ID NO: 11. Antibody molecules are preferably human or humanised antibody molecules. The L19-huTNFα conjugate may comprise or consist of the amino acid sequence set out in SEQ ID NO: 13.

Also described is a method comprising formulating the immunoconjugate or immunoconjugates into a pharmaceutical composition. Generally, this involves purifying the immunoconjugate or immunoconjugates and combining it with a physiologically acceptable carrier.

Immunoconjugates and compositions in accordance with the present invention may comprise, in addition to the active ingredient (immunoconjugate), a pharmaceutically acceptable excipient, carrier, buffer, stabiliser or other materials well known to those skilled in the art. Such materials should be non-toxic and should not interfere with the efficacy of the active ingredient. For injection at the tumour site, the immunoconjugate may be in the form of a parenterally acceptable aqueous solution which is pyrogen-free and has suitable pH, isotonicity and stability.

The therapeutic uses and methods described herein can be applied to different types of brain tumor. The tumor may be any unwanted cell proliferation (or any disease manifesting itself by unwanted cell proliferation), neoplasm or tumor. For instance, the brain tumor could be a primary malignant neoplasm of brain, a secondary malignant neoplasm of brain, a secondary malignant neoplasm of brain and cerebral meninges, a benign neoplasm of brain and central nervous system or a neoplasm of uncertain behaviour of brain. The neoplasm may be a glioma.

Some embodiments of this invention involve the use of the TNF immunoconjugate administered in combination with chemotherapy. Chemotherapy may be based on alkylating agents such as, chlorambucil, melphalan, cyclophosphamide, chlormethine, uramustine, ifosfamide, bemdamustine, carmustine, lomustine, streptozocin, busulfan, procarbazine, dacarbazine and temozolomide. Chemotherapy may be also based on alkylating-like agents such as cisplatin, carboplatin, dicycloplatin, eptaplatin, lobaplatin, miriplatin, nedaplatin, oxalilatin, picoplatin, satraplatin, Some embodiments of this invention involve the use of the TNF immunoconjugate formulated as a pharmaceutical composition. Pharmaceutical compositions may include a pharmaceutically acceptable "excipient" composed of materials that are considered safe and effective. "Pharmaceutically acceptable" refers to molecular entities and compositions that are "generally regarded as safe", e.g., that are physiologically tolerable and do not typically produce an allergic or similar untoward reaction, such as gastric upset and the like, when administered to a human. The excipients may include solvents, solubility enhancers, suspending agents, buffering agents, isotonicity agents, antioxidants or antimicrobial preservatives. Certain compositions of L19-TNFα are disclosed in WO2018/011404.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the description and examples should not be construed as limiting.

The present invention is illustrated by the following examples.

EXAMPLES

Example 1—Effect of L19-TNFα on Brain Tumour

Figure 1A:
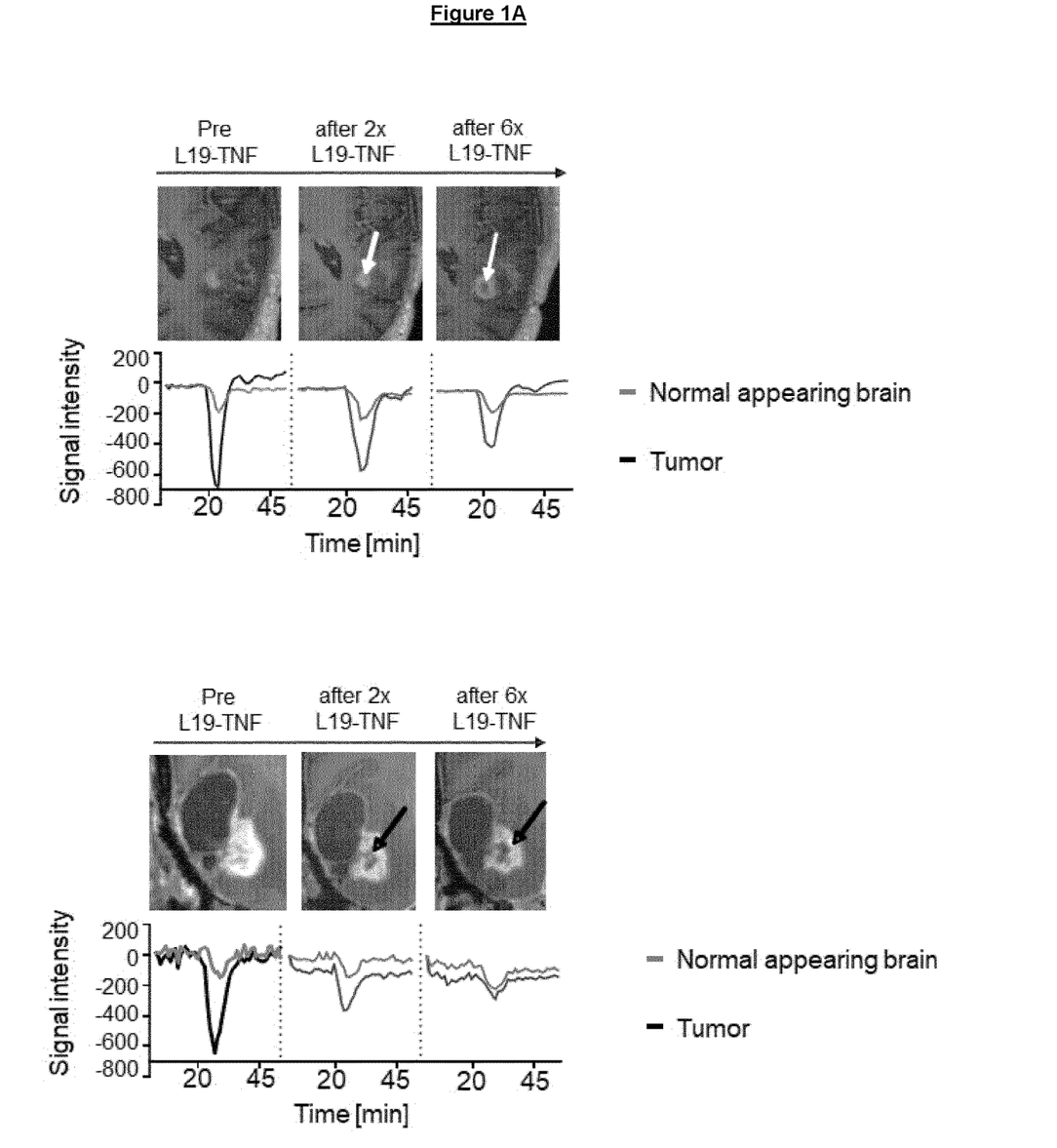
FIG. 1A shows glioma lesions in two different patients before and after treatment with L19-TNFα. The lesions gradually shrink after two and six cycles. The dark inner part of the lesions indicates the expanding necrotic core, confirming the therapeutic action of targeted TNFα.

Three patients with recurrent glioblastoma were treated with L19-TNFα at a dose level of 10 µg/kg. Already twenty-four hours after the infusion, a decrease in overall tumor perfusion and an emerging tumor necrosis was detected, as shown in FIG. 1A. One patient had progressive disease after three months and two patients still have stable disease with an increasing area of necrosis in the tumor region at six months after treatment. This is surprising considering that the Progression Free Survival (PFS) for recurrent glioblastoma is 1.5 months.

Figure 1B:
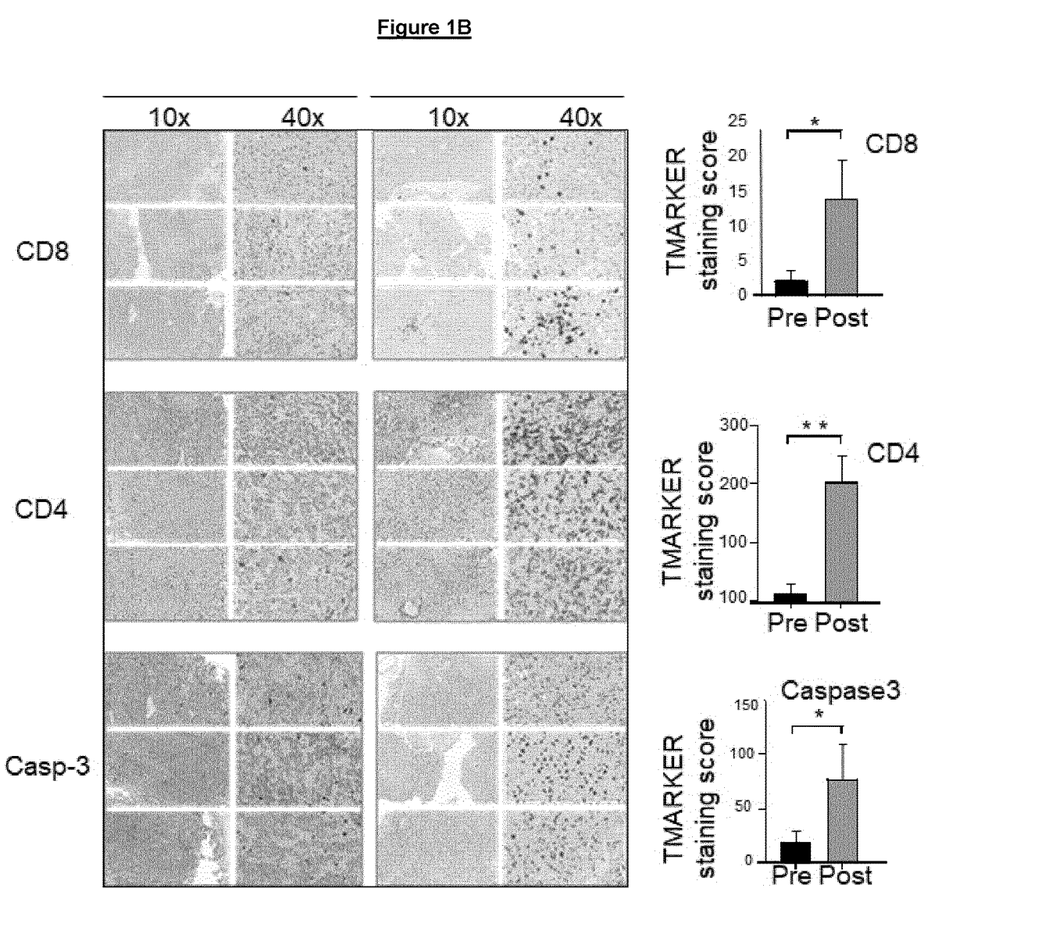
FIG. 1B Immunohistochemistry analysis before and after treatment with L19-TNFα. The increase in tumor-infiltrating CD4 and CD8 T-cells after treatment confirmed the therapeutic action of targeted TNFα. Similarly, the increase of caspase-3 indicates a higher number of dead tumor cells.

The patient with progressive disease underwent re-section and the tissue from this surgery, i.e. after treatment with L19-TNFα, was compared with the tissue obtained during first surgery. By immunohistochemistry, a significant increase in tumor-infiltrating CD4 and CD8 T-cells in the tumor after L19-TNFα treatment was detected. Furthermore, increased levels of cleaved caspase-3 were found suggesting a higher number of dead tumor cells, as shown in FIG. 1B. These data demonstrate the in situ activation due to the targeted delivery of TNF.

Example 2—Effect of L19-TNFα with Chemotherapy on Brain Tumour

This example describes the effect of a combination therapy on a patient with recurrent glioblastoma after chemoradiotherapy followed by temozolomide maintenance therapy.

A 61-year old male patient with glioblastoma (WHO grade IV) at first recurrence, received 90 mg/m2 lomustine (CCNU) on Day 1. Additionally, this patient received 13 µg/kg L19-TNF, by iv infusion, on Days 1, 3, 5, 22, 24 and 26.

The patient had been pretreated for newly diagnosed glioblastoma with resection and chemoradiotherapy followed by temozolomide maintenance therapy.

Figure 3:
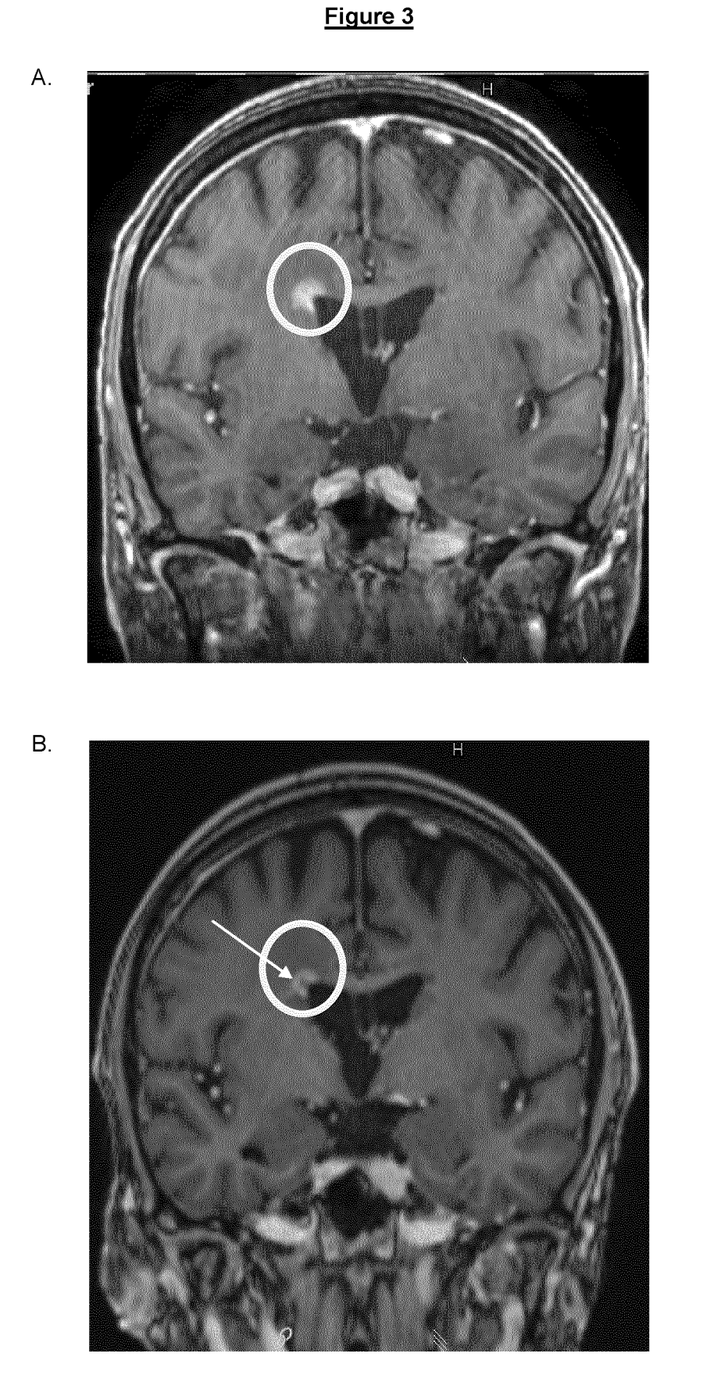
FIG. 3 shows MRI images of a glioblastoma patient who was administered L19-TNF in accordance with the invention. The upper panel (A) is the initial (baseline) MRI image, which shows the glioblastoma indicated in the white circle. The lower panel (B) shows an MRI image taken following treatment, 40 days after the baseline image was taken. The glioblastoma shown in panel B is indicated with an arrow and white circle. It is substantially reduced.

Contrast enhanced MRI was performed initially, before receiving the lomustine and L19-TNF (baseline image; see FIG. 3A) and 40 days after baseline image (FIG. 3B). The tumour was substantially reduced.

Numbered Paragraphs

1. A TNFα immunoconjugate for use in a method of treating a brain tumor in a patient, the method comprising administering the TNFα immunoconjugate to the patient.
2. The TNFα immunoconjugate for the use according to paragraph 1, wherein the brain tumor is a glioma.
3. The TNFα immunoconjugate for the use according to any one of the preceding paragraphs, wherein the TNFα immunoconjugate comprises TNFα linked to an antibody molecule that binds to a splice isoform of an extracellular matrix component.
4. The TNFα immunoconjugate for the use according to any one of the preceding paragraphs, wherein the antibody molecule binds a splice isoform of fibronectin which is B-FN.
5. The TNFα immunoconjugate for the use according to any one of the preceding paragraphs, wherein the TN Fa immunoconjugate comprises TN Fa linked to an antibody molecule comprising L19 complementarity determining regions (CDRs), wherein the L19 CDRs are:

|  |  | |
|---|---|---|
| VH CDR 1 | SFSMS | SEQ ID NO: 1 |
| VH CDR 2 | SISGSSGTTYYADSVKG | SEQ ID NO: 2 |
| VH CDR 3 | PFPYFDY | SEQ ID NO: 3 |
| VL CDR 1 | RASQSVSSSFLA | SEQ ID NO: 4 |
| VL CDR 2 | YASSRAT | SEQ ID NO: 5 |
| VL CDR 3 | QQTGRIPPT. | SEQ ID NO: 6 |

6. The TNFα immunoconjugate for the use according to paragraph 5, wherein the antibody molecule comprises the L19 VH domain SEQ ID NO: 7 and the L19 VL domain SEQ ID NO: 9.
7. The TNFα immunoconjugate for the use according to any one of the preceding paragraphs, wherein the TNFα immunoconjugate comprises TN Fa linked to an antibody molecule which is a scFv, optionally wherein the antibody molecule is L19 (scFv) as set forth in SEQ ID NO: 10.
8. The TNFα immunoconjugate for the use according to any one of the preceding paragraphs, wherein the TNFα immunoconjugate has an amino acid sequence of SEQ ID NO: 13.
9. The TNFα immunoconjugate for the use according to any one of the preceding paragraphs, wherein the immunoconjugate is administered by intravenous injection.
10. The TNFα immunoconjugate for the use according to paragraph 9, wherein the injection is intratumoural injection or intrathecal injection.
11. The TNFα immunoconjugate for the use according to any one of the preceding paragraphs, wherein the brain tumor is a Grade III/IV glioma.
12. The TNFα immunoconjugate for the use according to paragraph 11, wherein the glioma is isocitrate dehydrogenase (IDH) wildtype.
13. The TNFα immunoconjugate for the use according to paragraph 11 or paragraph 12, wherein the Grade III/IV glioma is at first relapse.
14. The TNFα immunoconjugate for the use according to paragraph 11 or paragraph 12, wherein the glioma is a Grade IV glioblastoma, which is newly diagnosed.
15. The TNFα immunoconjugate for the use according to any one of paragraphs 11 to 13, wherein the glioma is a Grade IV glioblastoma at first relapse.
16. The TNFα immunoconjugate for the use according any of the preceding paragraphs, wherein the immunoconjugate is administered in combination with chemotherapy and/or radiotherapy.
17. The TNFα immunoconjugate for the use according to paragraph 16, wherein the chemotherapy is the alkylating agent temozolomide (TMZ).
18. The TNFα immunoconjugate for the use according to paragraph 17, wherein temozolomide (TMZ) is administered at 75-200 mg/m².
19. The TNFα immunoconjugate for the use according to paragraph 17 or paragraph 18, wherein the radiotherapy is administered at a dose of 20-100 Gy, 40-80 Gy, or 60 Gy,
20. The TNFα immunoconjugate for the use according to paragraph 19, wherein the radiotherapy is administered at a dose of 60 Gy in fractions, preferably 60 Gy/30 fractions.
21. The TNFα immunoconjugate for the use according to paragraph 19 or 20, wherein the glioma is a newly diagnosed glioblastoma.
22. The TNFα immunoconjugate for the use according to paragraph 16, wherein the chemotherapy is the alkylating agent lomustine.
23. The TNFα immunoconjugate for the use according to paragraph 21, wherein lomustine is administered at a dose that is within the range of 50-200 mg/m², or 75-150 mg/m².
24. The TNFα immunoconjugate for the use according to paragraph 22, wherein the lomustine is administered at a dose of about 80, about 90, about 100, or about 110 mg/m².
25. The TNFα immunoconjugate for the use according to paragraph 22 or 23, wherein lomustine is administered at 90 mg/m².
25. The TNFα immunoconjugate for the use according to any one of paragraphs 22-25, wherein the glioblastoma is at first relapse.
26. The TNFα immunoconjugate for the use according to any one of the preceding paragraphs, wherein the method comprises subsequent administrations of the TNFα immunoconjugate.
27. The TNFα immunoconjugate for the use according any of the preceding paragraphs, wherein tumor necrosis is detectable one day after the TNFα immunoconjugate is administered to the patient.
28. The TNFα immunoconjugate for the use according any of the preceding paragraphs, wherein a reduction of blood perfusion to the tumor is detectable one day after the TNFα immunoconjugate is administered to the patient.

29. The TNFα immunoconjugate for the use according any of the preceding paragraphs, wherein the method induces infiltration of T cells into the tumor.

SEQUENCE LISTING

```
Amino acid sequence of L19 CDRs
L19 CDR1 VH
                                        (SEQ ID NO: 1)
SFSMS L19 CDR2 VH
                                        (SEQ ID NO: 2)
SISGSSGTTYYADSVKG

L19 CDR3 VH
                                        (SEQ ID NO: 3)
PFPYFDY

L19 CDR1 VL
                                        (SEQ ID NO: 4)
RASQSVSSSFLA

L19 CDR2 VL
                                        (SEQ ID NO: 5)
YASSRAT

L19 CDR3 VL
                                        (SEQ ID NO: 6)
QQTGRIPPT

Amino acid sequence of the L19 VH domain
                                        (SEQ ID NO: 7)
EVQLLESGGGLVQPGGSLRLSCAASGFTFSSFSMSWVRQAPGKGLEWVSS

ISGSSGTTYYADSVKGRFTISRDNSKNTLYLQMNSLRAEDTAVYYCAKPF

PYFDYWGQGTLVTVSS

Amino acid sequence of the linker between VH and
VL
                                        (SEQ ID NO: 8)
GDGSSGGSGGAS Amino acid sequence of the L19 VL domain
                                        (SEQ ID NO: 9)
EIVLTQSPGTLSLSPGERATLSCRASQSVSSSFLAWYQQKPGQAPRLLIY

YASSRATGIPDRFSGSGSGTDFTLTISRLEPEDFAVYYCQQTGRIPPTFG

QGTKVEIK

Amino acid sequence of the L19 scFv
                                        (SEQ ID NO: 10)
EVQLLESGGGLVQPGGSLRLSCAASGFTFSSFSMSWVRQAPGKGLEWVSS

ISGSSGTTYYADSVKGRFTISRDNSKNTLYLQMNSLRAEDTAVYYCAKPF

PYFDYWGQGTLVTVSSGDGSSGGSGGASEIVLTQSPGTLSLSPGERATLS

CRASQSVSSSFLAWYQQKPGQAPRLLIYYASSRATGIPDRFSGSGSGTDF

TLTISRLEPEDFAVYYCQQTGRIPPTFGQGTKVEIK

Amino acid sequence of the soluble form of the
extracellular domain of human TNFα (huTNFα).
                                        (SEQ ID NO: 11)
VRSSSRTPSDKPVAHVVANPQAEGQLQWLNRRANALLANGVELRDNQLVV

PSEGLYLIYSQVLFKGQGCPSTHVLLTHTISRIAVSYQTKVNLLSAIKSP

CQRETPEGAEAKPWYEPIYLGGVFQLEKGDRLSAEINRPDYLDFAESGQV

YFGIIAL

Amino acid sequence of the linker between scFv and
TNF
                                        (SEQ ID NO: 12)
EFSSSSGSSSSGSSSG Amino acid sequence of the L19-huTNF conjugate
                                        (SEQ ID NO: 13)
EVQLLESGGGLVQPGGSLRLSCAASGFTFSSFSMSWVRQAPGKGLEWVSS

ISGSSGTTYYADSVKGRFTISRDNSKNTLYLQMNSLRAEDTAVYYCAKPF

PYFDYWGQGTLVTVSSGDGSSGGSGGASEIVLTQSPGTLSLSPGERATLS

CRASQSVSSSFLAWYQQKPGQAPRLLIYYASSRATGIPDRFSGSGSGTDF

TLTISRLEPEDFAVYYCQQTGRIPPTFGQGTKVEIKEFSSSSGSSSSGSS

SSGVRSSSRTPSDKPVAHVVANPQAEGQLQWLNRRANALLANGVELRDNQ

LVVPSEGLYLIYSQVLFKGQGCPSTHVLLTHTISRIAVSYQTKVNLLSAI

KSPCQRETPEGAEAKPWYEPIYLGGVFQLEKGDRLSAEINRPDYLDFAES

GQVYFGIIAL
```

The invention claimed is:

1. A method of treating a brain tumor in a patient, comprising administering a TNFα immunoconjugate in combination with chemotherapy to the patient, wherein the TNFα immunoconjugate comprises TNFα linked to an antibody molecule comprising L19 complementarity determining regions (CDRs), wherein the L19 CDRs are:

| | | |
|---|---|---|
| VH CDR1 | SFSMS | SEQ ID NO: 1 |
| VH CDR 2 | SISGSSGTTYYADSVKG | SEQ ID NO: 2 |
| VH CDR 3 | PFPYFDY | SEQ ID NO: 3 |
| VL CDR 1 | RASQSVSSSFLA | SEQ ID NO: 4 |
| VL CDR 2 | YASSRAT, and | SEQ ID NO: 5 |
| VL CDR 3 | QQTGRIPPT; | SEQ ID NO: 6 | and the chemotherapy is lomustine, wherein said combination increases brain tumor necrosis and Progression Free Survival (PFS) in said patient and said brain tumor is a glioma.

2. The method of claim 1, wherein the antibody molecule comprises the L19 VH domain SEQ ID NO: 7 and the L19 VL domain SEQ ID NO: 9.

3. The method of 1, wherein the TNFα immunoconjugate comprises TNFα linked to L19 (scFv) as set forth in SEQ ID NO: 10.

4. The method of any one of claim 1, 2, or 3, wherein the TNFα immunoconjugate has an amino acid sequence of SEQ ID NO: 13.

5. The method of claim 1, wherein the immunoconjugate is administered by a route selected from intravenous injection, intratumoural injection, and intrathecal injection.

6. The method of claim 1, wherein the glioma is selected from a Grade III/IV glioma, a Grade III/IV glioma is at first relapse, an isocitrate dehydrogenase (IDH) wildtype glioma, a newly diagnosed Grade IV glioblastoma, and a Grade IV glioblastoma at first relapse.

7. The method of claim 1, wherein the immunoconjugate is administered in combination with radiotherapy.

8. The method of claim 1, wherein lomustine is administered at a dose in a range of 50-200 mg/m$^2$, or 75-150 mg/m$^2$.

9. The method of claim 1, wherein the lomustine is administered at a dose of about 80, about 90, or about 100, or about 110 mg/m$^2$.

10. The method of claim 1, further comprising subsequent administrations of the TNFα immunoconjugate.

11. A method of treating a glioma in a patient, comprising administering a TNFα immunoconjugate in combination with chemotherapy to the patient, wherein the TNFα immunoconjugate comprises TNFα linked to an antibody molecule comprising L19 complementarity determining regions (CDRs), wherein the L19 CDRs are:

| | | |
|---|---|---|
| VH CDR1 | SFSMS | SEQ ID NO: 1 |
| VH CDR 2 | SISGSSGTTYYADSVKG | SEQ ID NO: 2 |
| VH CDR 3 | PFPYFDY | SEQ ID NO: 3 |
| VL CDR 1 | RASQSVSSSFLA | SEQ ID NO: 4 |
| VL CDR 2 | YASSRAT, and | SEQ ID NO: 5 |
| VL CDR 3 | QQTGRIPPT; | SEQ ID NO: 6 | wherein the chemotherapy is lomustine;
wherein the antibody molecule comprises the L19 VH domain SEQ ID NO: 7 and the L19 VL domain SEQ ID NO: 9;
wherein the TNFα immunoconjugate comprises TNFα linked to L19 (scFv) as set forth in SEQ ID NO: 10 and the TNFα immunoconjugate has an amino acid sequence of SEQ ID NO: 13.

12. The method of claim 11, wherein the immunoconjugate is administered by a route selected from intravenous injection, intratumoural injection, and intrathecal injection.

13. The method of claim 11, wherein said glioma is selected from a Grade III/IV glioma, a Grade III/IV glioma is at first relapse, an isocitrate dehydrogenase (IDH) wild-type glioma, a newly diagnosed Grade IV glioblastoma, and a Grade IV glioblastoma at first relapse.

14. The method of claim 11, further comprising administration of radiotherapy.

15. The method of claim 11, wherein the lomustine is administered at a dose in a range of 50-200 mg/m$^2$, or 75-150 mg/m$^2$.

16. The method of claim 11 further comprising subsequent administrations of the TNFα immunoconjugate.

* * * * *